(12) United States Patent
Aoki et al.

(10) Patent No.: US 6,926,601 B2
(45) Date of Patent: Aug. 9, 2005

(54) APPARATUS AND METHOD FOR DEODORIZING COMPARTMENT OF VEHICLE

(75) Inventors: Shinji Aoki, Chiryu (JP); Shinji Iwama, Nagoya (JP)

(73) Assignee: DENSO Corporation, Kariya (JP)

( * ) Notice: Subject to any disclaimer, the term of this patent is extended or adjusted under 35 U.S.C. 154(b) by 132 days.

(21) Appl. No.: 10/646,557

(22) Filed: Aug. 21, 2003

(65) Prior Publication Data

US 2004/0053571 A1 Mar. 18, 2004

(30) Foreign Application Priority Data

Aug. 28, 2002 (JP) ........................................ 2002-248833

(51) Int. Cl.⁷ ................................................ B60S 1/54
(52) U.S. Cl. ........................................ 454/121; 454/256
(58) Field of Search .................. 454/121, 75, 256, 454/143; 165/41, 42

(56) References Cited

U.S. PATENT DOCUMENTS

| | | | | |
|---|---|---|---|---|
| 3,750,556 A | * | 8/1973 | Duke et al. ................. 454/159 |
| 4,407,354 A | * | 10/1983 | Takishita et al. ............. 165/42 |
| 4,494,597 A | * | 1/1985 | Fukami et al. ................ 165/41 |
| 4,593,609 A | * | 6/1986 | Nagatomo et al. ............ 454/75 |
| 4,702,753 A | * | 10/1987 | Kowalczyk ................ 96/117.5 |
| 4,711,159 A | * | 12/1987 | Armbruster ................ 454/137 |
| 5,099,752 A | * | 3/1992 | Bosley ........................ 454/131 |
| 5,681,218 A | * | 10/1997 | Kishi et al. .................... 454/75 |
| 5,876,277 A | * | 3/1999 | Uemura et al. ............. 454/139 |
| 6,623,350 B2 | * | 9/2003 | Goupil et al. ................ 454/158 |
| 6,758,739 B1 | * | 7/2004 | Sangwan et al. ............. 454/75 |

FOREIGN PATENT DOCUMENTS

| | | |
|---|---|---|
| JP | 59-51451 | 12/1984 |
| JP | 7-55614 | 6/1995 |

* cited by examiner

Primary Examiner—Derek S. Boles
(74) Attorney, Agent, or Firm—Harness, Dickey & Pierce, PLC

(57) ABSTRACT

In a deodorizing apparatus for a vehicular passenger compartment, when an ignition key is off and it is determined that a density of odor components in the passenger compartment is equal to or higher than a predetermined level, it is determined whether an inside temperature inside the passenger compartment measured by a temperature sensor is equal to or higher than a predetermined temperature, which is suitable for separating odor components adhered to the passenger compartment. When it is determined that the inside temperature is equal to or higher than the predetermined temperature, a deodorizing operation is performed by a deodorizing means. When it is determined that the inside temperature is lower than the predetermined temperature and it is not assumed that the inside temperature naturally increases to the predetermined temperature, the passenger compartment is heated by a compartment heating device so that the inside temperature reaches the predetermined temperature.

15 Claims, 7 Drawing Sheets

APPARATUS AND METHOD FOR DEODORIZING COMPARTMENT OF VEHICLE

CROSS REFERENCE TO RELATED APPLICATION

This application is based on Japanese Patent Application No. 2002-248833 filed on Aug. 28, 2002, the disclosure of which is incorporated herein by reference.

FIELD OF THE INVENTION

The present invention relates to an apparatus and a method for deodorizing a passenger compartment of a vehicle.

BACKGROUND OF THE INVENTION

According to ventilating apparatus disclosed in JP-B2-59-51451 and JP-B2-7-55614, for example, a passenger compartment is ventilated by using a solar battery while the vehicle is stopped. With this, the passenger compartment is deodorized.

Generally, odor components such as tobacco smoke adhere to interior parts, such as an instrument panel, a steering wheel and a seat, in the passenger compartment. The extrication of such odor components from the interior parts results in odor in the passenger compartment. An adhesive agent, which is used for fixing the interior parts, also results in the odors.

With regard to a seat of the vehicle, a backing material is generally applied to a rear surface of a seat cover member for reducing removal of fibers of the cover member. In some cases, activated carbon is added to the backing material. The activated carbon adsorbs odor components caused by such as passengers sweat and smell of tobacco smoke, thereby deodorizing the air in the passenger compartment. However, if the vehicle is parked under the blazing sun, deodorizing capacity of the activated carbon is saturated. As a result, the odor components are extricated from the activated carbon. Thus, the deodorant such as the activated carbon is likely to cause the odor in the compartment adversely.

In a case that the odor components are strongly adhered to the interior parts, the odor components are not easily extricated into the air inside the compartment. Further, the extrication of the odor components deteriorates under the low temperature. In such circumstances, it is difficult to sufficiently eliminate the odor components from the passenger compartment merely by ventilation and air cleaning.

SUMMARY OF THE INVENTION

It is an object of the present invention to provide a deodorizing apparatus capable of eliminating odor components in a passenger compartment of a vehicle under a temperature suitable for separating odor components from an interior of the passenger compartment.

It is another object of the present invention to provide a method for deodorizing a passenger compartment of a vehicle under a temperature suitable for separating odor components from an interior of the passenger compartment.

According to an aspect of the present invention, a deodorizing apparatus for a passenger compartment of a vehicle includes a temperature sensor, a deodorizing means, a compartment heating device, a deodorizing operation control means, and a heating operation control means. The temperature sensor measures an inside temperature inside the passenger compartment. When the vehicle is parked and the measured inside temperature is equal to or higher than a predetermined temperature, the deodorizing operation control means controls the deodorizing means to remove odor components inside the passenger compartment. When the vehicle is parked and the measured inside temperature is lower than the predetermined temperature, the heating operation control means controls the heating device so that the inside temperature reaches the predetermined temperature. The predetermined temperature is a reference for determining whether the inside temperature reaches a temperature suitable for separating odor components adhered to the interior of the passenger compartment.

Accordingly, when the vehicle is parked and the measured inside temperature is equal to or higher than the predetermined temperature, a deodorizing operation is performed by the deodorizing means. When the vehicle is parked and the measured inside temperature is lower than the predetermined temperature, a heating operation is performed by the compartment heating device. Therefore, the passenger compartment is deodorized under the temperature suitable for separating the odor components adhered to the interior of the passenger compartment.

According to another aspect of the present invention, a deodorizing apparatus for a passenger compartment of a vehicle includes an estimating means, a deodorizing means, and a deodorizing operation control means. The estimating means estimates a timing that an inside temperature inside the passenger compartment reaches a predetermined temperature for separating odor components adhered to the interior of the passenger compartment. The deodorizing operation control means controls the deodorizing means so that the deodorizing means starts to remove the odor components inside the passenger compartment at the timing, while the vehicle is parked.

Accordingly, the deodorizing means starts deodorization at the timing when the inside temperature reaches the predetermined temperature while the vehicle is parked. Thus, the passenger compartment is deodorized under the temperature suitable for separating the odor components adhered to the interior of the passenger compartment.

According to a method for deodorizing a passenger compartment of a vehicle of the present invention, it is determined whether a measured inside temperature inside the passenger compartment is equal to or higher than a predetermined temperature while the vehicle is parked. If it is determined that the measured inside temperature is equal to or higher than the predetermined temperature, a deodorizing means is controlled to remove odor components in the passenger compartment. If it is determined that the measured inside temperature is lower than the predetermined temperature, a heating device is controlled to heat the passenger compartment so that the inside temperature reaches the predetermined temperature.

According to another method for deodorizing a passenger compartment of a vehicle of the present invention, a timing that an inside temperature inside the passenger compartment reaches a predetermined temperature is estimated while the vehicle is parked. Then, a deodorizing means is controlled to start to remove odor components inside the passenger compartment at the timing.

Accordingly, the passenger compartment is deodorized under the temperature suitable for separating odor components adhered to the interior of the passenger compartment.

BRIEF DESCRIPTION OF THE DRAWINGS

Other objects, features and advantages of the present invention will become more apparent from the following detailed description made with reference to the accompanying drawings, in which like parts are designated by like reference numbers and in which.

DETAILED DESCRIPTION OF EMBODIMENTS

Embodiments of the present invention will be described hereinafter with reference to drawings.

[First Embodiment]

Figure 1:
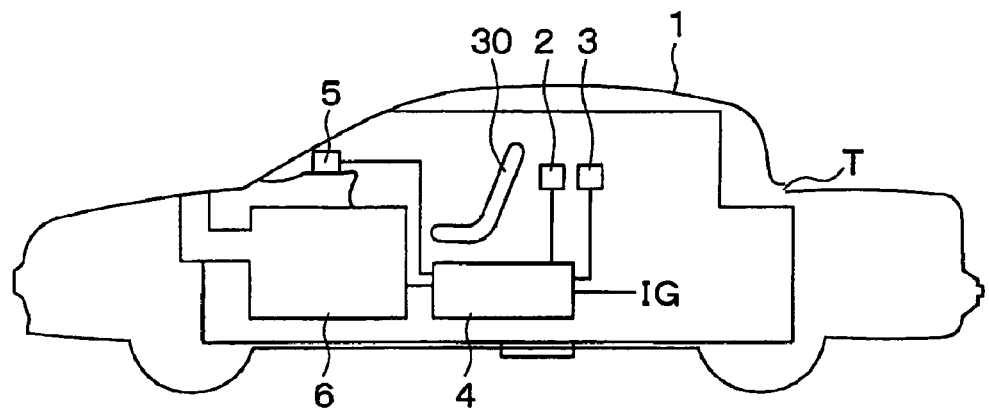
FIG. 1 is a schematic diagram showing an arrangement of a deodorizing apparatus on a vehicle according to the first embodiment of the present invention.

Referring to FIG. 1, a deodorizing apparatus for a passenger compartment of a vehicle 1 is constructed of a temperature sensor 2, an odor sensor 3, a controller 4, a solar radiation sensor 5, an air conditioning unit 6 and a seat 30.

The temperature sensor 2 is for example constructed of thermister and measures an inside temperature Ti inside of the passenger compartment. The odor sensor 3 is located on the ceiling on the top of the driver's seat. The odor sensor 3 measures a density Di of odor components, such as HC, CO, $NO_x$, and $CO_2$, extricating in the compartment. The solar radiation sensor 5 measures an amount SRi of solar radiation incoming into the compartment.

The controller 4 includes a CPU, a RAM, and a ROM (not shown). The CPU interprets programs stored in the ROM and performs various tasks in accordance with the programs. Further, the CPU writes and reads information to and from the RAM as required for the tasks. Also, thresholds of such as an inside temperature, the amount of solar radiation, a density of components are stored on the ROM. These thresholds will be described later in detail.

The controller 4 receives signals with respect to information about physical values measured by the respective sensors 2, 3, 5. The controller 4 controls motors of the air conditioning unit 6, blower units and electric heaters installed in the seat 30. Also, the controller 4 determines ON, ACC, and OFF positions of an ignition key through signal wires.

Figure 2:
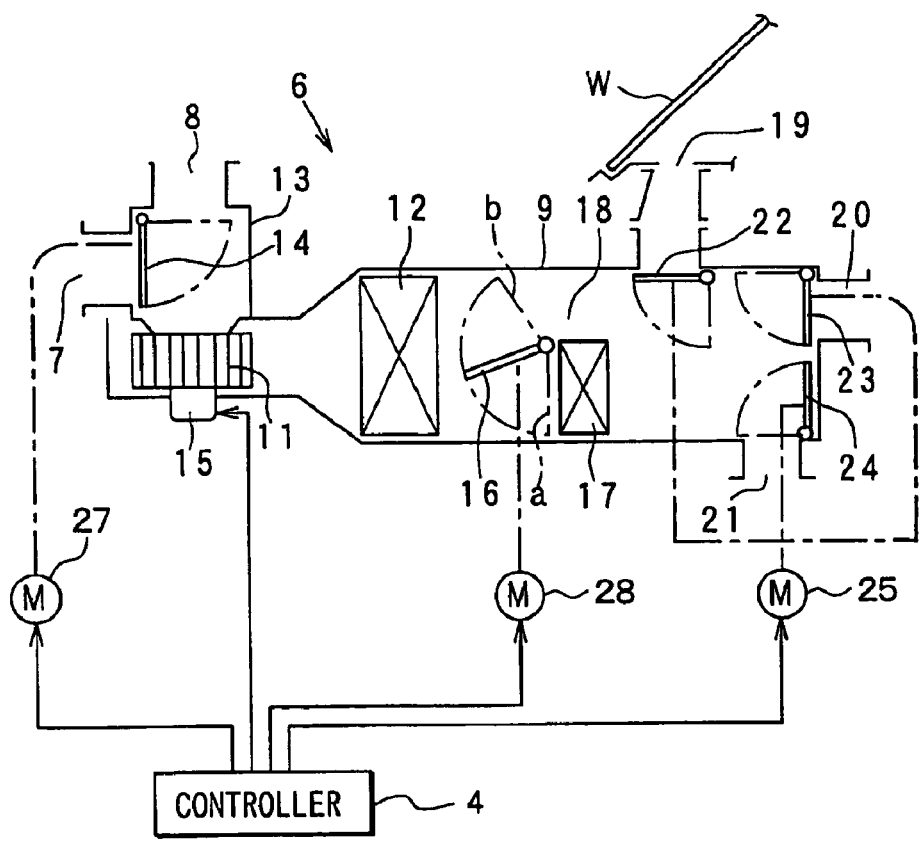
FIG. 2 is a schematic diagram of a ventilation system of an air conditioning unit according to the first embodiment of the present invention.

As shown in FIG. 2, the air conditioning unit 6 has a case 9 defining an air passage through which air flows into the passenger compartment. An inside/outside air switching box 13 is arranged at a most upstream position of the air passage in the case 9. The box 13 forms an outside air introduction port 7 through which outside air outside the passenger compartment is introduced and an inside air introduction port 8 through which inside air inside the passenger compartment is introduced. An inside/outside air switching door 14 is rotatably supported in the box 13. The door 14 is driven by a servomotor 27 so that the door 14 switches between an inside air mode, which draws the inside air from the inside air introduction port 8, and an outside air mode, which draws the outside air from the outside air introduction port 7.

A centrifugal fan 11 is arranged at a downstream position in the box 13. The fan 11 creates a flow of air toward the passenger compartment. The fan 11 is driven by a motor 15. An evaporator 12 is arranged downstream of the fan 11 in the case 9. The evaporator 12 is controlled by the controller 4. The evaporator 12 is a heat exchanger for cooling the air flowing from the fan 11 by a refrigerant cycle system (not shown).

A heater core 17 is arranged downstream of the evaporator 12 in the case 9. The heater core 17 is a heat exchanger for performing heat exchange between engine coolant and the air, which has been cooled by the evaporator 12, thereby heating the air. The case 19 defines a bypass passage 18 next to the heater core 17 so that the air, which has passed through the evaporator 12, bypasses the heater core 17.

An air mixing door 16 is rotatably provided between the evaporator 12 and the heater core 17 in the case 9. The air mixing door 16 is driven by a servomotor 28 so that its position, that is, its opening degree is continuously adjusted. A flow rate of the air flowing in the heater core 17 to be heated and a flow rate of the cold air bypassing the heater core 17 are adjusted by the opening degree of the door 16, so that the temperature of the air blown into the passenger compartment is controlled.

The case 9 forms a defroster air-blowing port 19 through which the conditioned air is blown toward a windshield W, a face air-blowing port 20 through which the conditioned air is blown toward the upper half of a passenger body, and a foot air-blowing port 21 through which the conditioned air is blown toward the lower half of the passenger body. The air-blowing ports 19, 20, 21 are located at the most air downstream position of the air passage in the case 9.

A defroster door 22, a face door 23, and a foot door 24 are rotatably supported at the upstream positions of the defroster air-blowing port 19, the face air-blowing port 20, and the foot air-blowing port 21, respectively. The doors 22 to 24 are driven by a servomotor 25 through link mechanisms (not shown). The servomotors 25, 27, 28 and the motor 15 are controlled by the controller 4.

Figure 3:
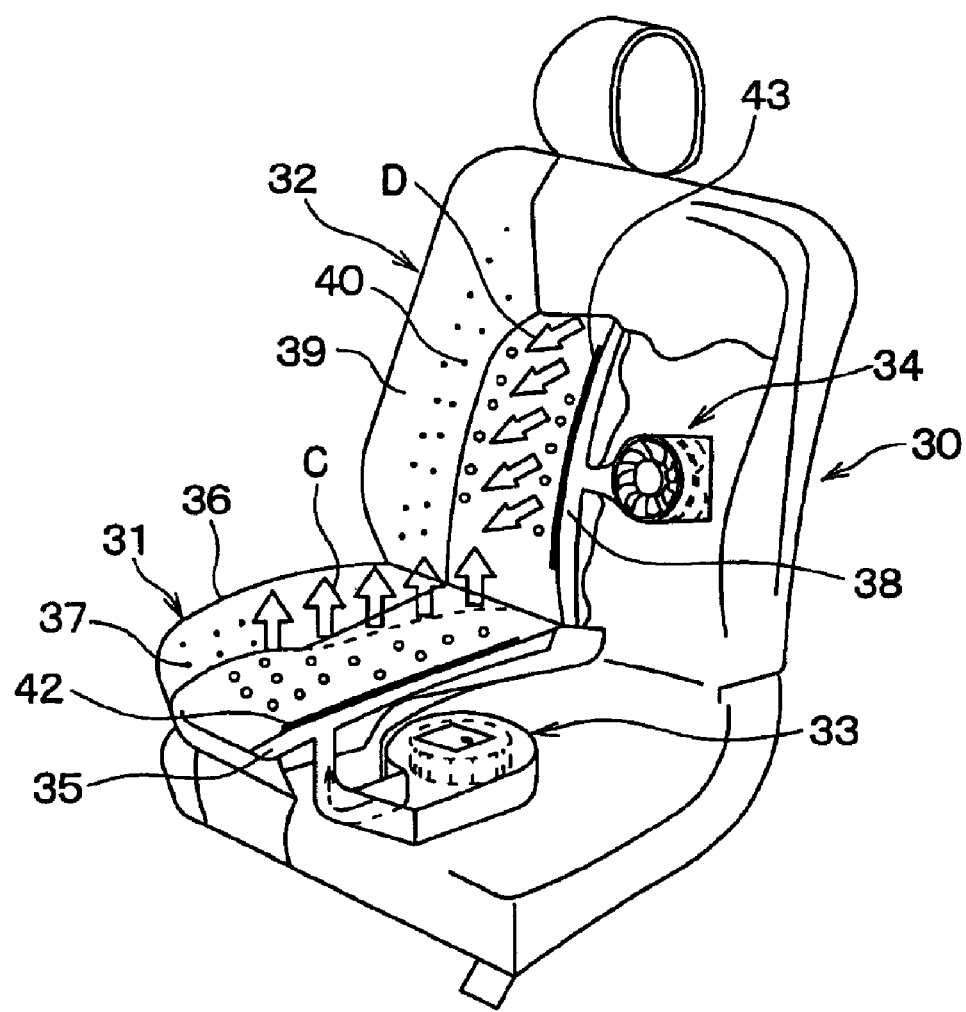
FIG. 3 is a perspective view of a seat for the vehicle according to the first embodiment of the present invention.

The seat shown in FIG. 3 is used for a driver seat and an assistant driver seats. A first blower unit 33 and a second blower unit 34 are respectively installed in a seat bottom 31 and a seat back 32 of the seat 30. The first blower unit 33 and the second blower unit 34 respectively have fans and electric motors for rotating the fans.

The first blower unit 33 is disposed such that its air intake port (not shown) is located at a lower position in the seat bottom 31. The first blower unit 33 draws the inside air from the air intake port and introduces the air toward a cover member 36 of the seat bottom 31 through an air passage 35. Thus, the air (conditioned air) is blown off toward the passenger through openings 37, which are formed on the cover member 36, as denoted by arrows C in FIG. 3.

The second blower unit 34 functions similar to the first blower unit 33. The second blower unit 34 is disposed such that its air intake port (not shown) is located at a lower position in the seat back 32. The second blower unit 34 draws the inside air from the air intake port and introduces the air toward a cover member 39 through an air passage 38 formed within the seat back 32. Thus, the air (conditioned air) is blown off toward the passenger through openings 40, which are formed on the cover member 39, as denoted by arrows D in FIG. 3.

In the seat bottom 31 and seat back 32, the electric heaters 42, 43 are arranged on the rear sides of the cover members 36, 39, respectively. The electric heaters 42, 43 are constructed of electric resistance wires and arranged in the form of meandering over wide areas of the seat bottom 31 and the seat back 32.

Thus, the cover members 36, 39, which make contact with the passenger, are directly heated by the electric heaters 42, 43 when the electric heaters 42, 43 are supplied with power. When the first and the second blower units 33, 34 are operated at the same time as heating the electric heaters 42, 43, the air heated by the heaters 42, 43 is blown toward the passenger through the openings 37, 40.

Figure 4:
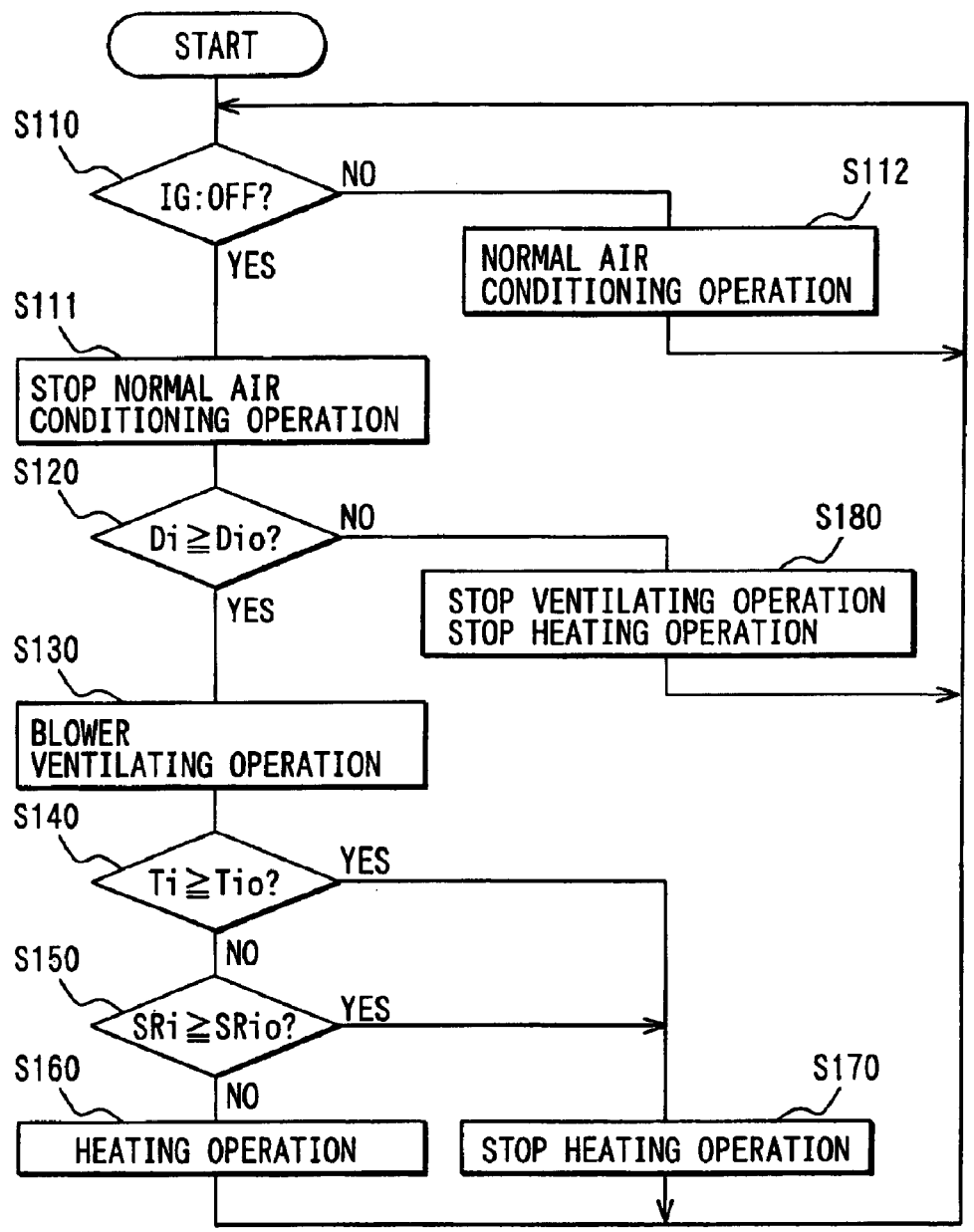
FIG. 4 is a flow chart showing a process of a controller according to the first embodiment of the present invention.

Next, the operation of the deodorizing apparatus will be described with reference to FIG. 4. FIG. 4 shows a flow chart of a loop program executed by the controller 4 during an operation of the controller 4. The controller 4 is always in an operating state by receiving power from a battery, irrespective of the ON and OFF conditions of the ignition key.

First, it is determined whether the ignition key is OFF at S110. When it is determined that the ignition key is OFF, it is determined that the vehicle 1 is parked.

If it is determined that the ignition key is not OFF, a normal air conditioning operation is performed at S112. In the normal air conditioning operation, the motor 15 is controlled to drive the fan 11. The servomotor 27 is controlled by receiving signals from switches (not shown), which are operated by the passenger, so that the inside/outside air switching door 14 is driven. Also, the servomotor 25 is controlled to drive the defroster door 22, the face door 23, and the foot door 24. The air mixing door 16 and the evaporator 12 are controlled based on the room temperature or the temperature set by the passenger. In this way, heating operation and cooling operation are performed in the normal air conditioning operation. While the ignition key is not OFF, the controls of S110 and S112 are repeated.

If it is determined that the ignition key is OFF at S110, the operations of the fan 11 and the evaporator 12 are stopped so that the normal air conditioning operation is stopped at S111 if it is performed at this time.

Next, it is determined whether an amount of odor in the passenger compartment is equal to or greater than a predetermined amount of odor at S120. Specifically, it is determined whether a density $D_i$ of odor components measured by the odor sensor 3 is equal to or higher than a predetermined density $D_{io}$ (e.g. normally between 2.0 ppm and 3.0 ppm).

If it is determined that the density $D_i$ is equal to or higher than the predetermined density $D_{io}$, the air conditioning unit 6 is controlled to perform a ventilating operation for deodorizing the air inside the compartment at S130. Specifically, the motor 27 is controlled to drive the inside/outside air switching door 14 to the outside air mode. The servomotor 25 is controlled to close the defroster door 22 and the foot door 24 and to open the face door 23. The motor 15 is controlled to drive the fan 11. Also, the first blower unit 33 and the second blower unit 34 are operated. As a result, the outside air is introduced from the outside air introduction port 7 and blown into the passenger compartment from the face air-blowing port 20. The air is discharged from a rear discharging port T (FIG. 1). In this way, the passenger compartment is ventilated by the air conditioning unit 6.

Next, it is determined whether an inside temperature $T_i$ measured by the inside air temperature sensor 2 is equal to or higher than a predetermined temperature $T_{io}$ (e.g. normally between 35° C. and 45° C.) at S140. The predetermined temperature $T_{io}$ is a reference for determining whether the inside temperature $T_i$ reaches a temperature suitable for separating the odor components adhered to the interior of the passenger compartment.

If it is determined that the inside temperature $T_i$ is lower than the predetermined temperature $T_{io}$, it is determined whether the amount $SR_i$ of solar radiation measured by the solar radiation sensor 5 is equal to or higher than a predetermined mount $SR_{io}$ (e.g. 150 W/m$^2$) at S150.

If it is determined that the amount $SR_i$ of solar radiation is less than the predetermined amount $SR_{io}$, the air conditioning unit 6 and the electric heaters 42, 43 are controlled to heat the passenger compartment and the seat 30 at S160. Specifically, the servomotor 28 is controlled to drive the air mixing door 16 at a position denoted by a chained line B in FIG. 2, so that the air blown by the fan 11 is entirely directed to the heater core 17 (maximum heating mode). The servomotor 27 is controlled to drive the inside/outside air switching door 14 to the outside air mode. The servomotor 25 is controlled to close the defroster door 22 and the foot door 24 and to open the face door 23. The motor 15 is controlled to drive the fan 11. Also, the heaters 42, 43 are controlled to generate heat. The first blower unit 33 and the second blower unit 34 are operated. Then, the control returns to the step S110.

In the loop program from S110, S120, S130, S140, S150, S160 to S110, the heating operations for heating the compartment and the seat 30 are performed at the same time as the ventilating operation, when the ignition key is OFF, the amount $D_i$ of odor components is equal to or higher than the predetermined amount $D_{io}$, the inside temperature $T_i$ is lower than the predetermined temperature $T_{io}$, and the amount $SR_i$ of solar radiation is lower than the predetermined amount $SR_{io}$.

If it is determined that the inside temperature $T_i$ is equal to or higher than the predetermined temperature $T_{io}$ at S140, the heating operation is stopped at S170 if it is performed. Thus, only the ventilating operation is performed at S170. Specifically, the servomotor 28 is controlled to fix the air mixing door 16 at the position denoted by chained line A in FIG. 2, so that the air blown by the fan 11 is entirely directed to the bypass passage 18 (maximum cooling mode). Also, the heating operations of the heater 42, 43 are stopped. The ventilating operation is performed in a manner similar to that of S130. Then, the control returns to the step S110. The reason why the heating operations are stopped at S170 is because the deodorizing effect can be achieved by the ventilating operation if the inside temperature is equal to or higher than the temperature suitable for separating odor components adhered to the interior.

Also, if it is determined that the amount $SR_i$ of solar radiation is equal to or greater than the predetermined amount $SR_{io}$ at S150, the heating operation is stopped at S170 if it is performed at this time. When the amount $SR_i$ of solar radiation is sufficient, the inside of the compartment is naturally heated by the solar radiation. Thus, the reason why the heating operation is stopped at S170 is because it is assumed that the temperature $T_i$ naturally increases to and reaches the predetermined temperature $T_{io}$ by the solar radiation in a predetermined period of time.

If it is determined that the density $D_i$ of the odor components measured by the odor sensor 3 is lower than the predetermined density $D_{io}$ at S120, the heating operation and the ventilating operation are stopped at S180 if those operations are performed. Specifically, the motor 15 is controlled to stop the operation of the fan 11. The electric heaters 42, 43 are controlled to stop the heating operations. At this time, the inside/outside air switching door 14, the air mixing door 16, the defroster door 22, the face door 23, and the foot door 24 can be at any positions or states. Then, the control returns to the step S110.

Accordingly, the passenger compartment is deodorized by the control of the controller 4 when the density Di of the odor components in the passenger compartment is equal to or higher than the predetermined density Dio and the inside temperature Ti is on the level suitable for removing the odor components adhered to the interior of the passenger compartment, while the ignition key is OFF. On the other hand, if the inside temperature Ti is lower than the predetermined temperature Tio and it is not assumed that the inside temperature Ti naturally increases to the predetermined temperature Tio, the heating operations are performed by a compartment heating device so that the temperature Ti reaches the suitable temperature. In this way, the passenger compartment is deodorized under the suitable temperature.

During the ventilating operation, extrication of the odor components, which are adhered to the seat 30, can be facilitated by the operations of the first blower unit 33 and the second blower unit 34. Also, during the heating operation, the seat 30 is heated by the heaters 42, 43. Thus, extrication of the odor components, which are adhered to the seat 30, can be facilitated by heat of the heaters 42, 43.

[Second Embodiment]

Figure 5:
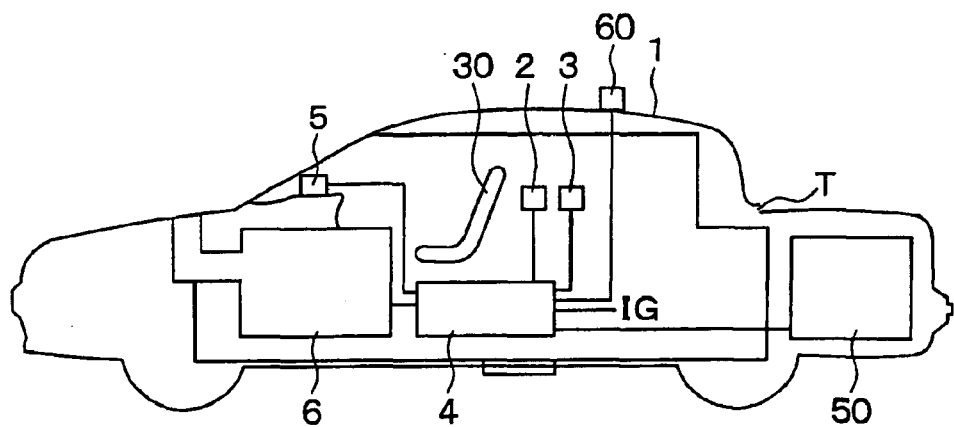
FIG. 5 is a schematic diagram showing an arrangement of a deodorizing apparatus on a vehicle according to the second embodiment of the present invention.

Referring to FIG. 5, in the second embodiment, the deodorizing apparatus further includes an air cleaner 50 and an outside air odor sensor 60. The air cleaner 50 is arranged on the rear side of the vehicle 1. The outside air odor sensor 60 measures a density Ds of odor components contained in air outside the vehicle 1. The controller 4 receives signals of information about physical values measured by the outside air odor sensor 60.

Figure 6:
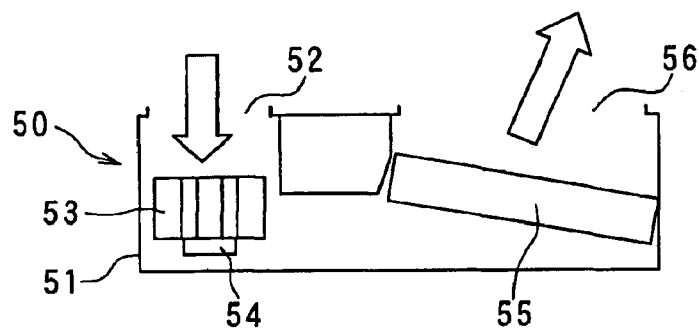
FIG. 6 is a schematic diagram of an air cleaner according to the second embodiment of the present invention.

As shown in FIG. 6, the air cleaner 50 has a cleaner case 51, a blower 53 and an electric motor 54. The case 51 has an inside air intake port 52 through which the inside air is introduced in the case 51 by the blower 53. The blower 53 is driven by the motor 54. The rotation of the motor 54 is controlled by the controller 4 so that operation of the air cleaner 50 is controlled.

In the case 51, a filter 55 is provided downstream of the blower 53. The filter 55 is constructed by joining deodorant, such as activated carbon for adsorbing odor components contained in the air, to a porous filter base material, such as urethane foam, by a binder. The air is blown into the passenger compartment from an air-blowing port 56 after filtered by the filter 55.

Figure 7:
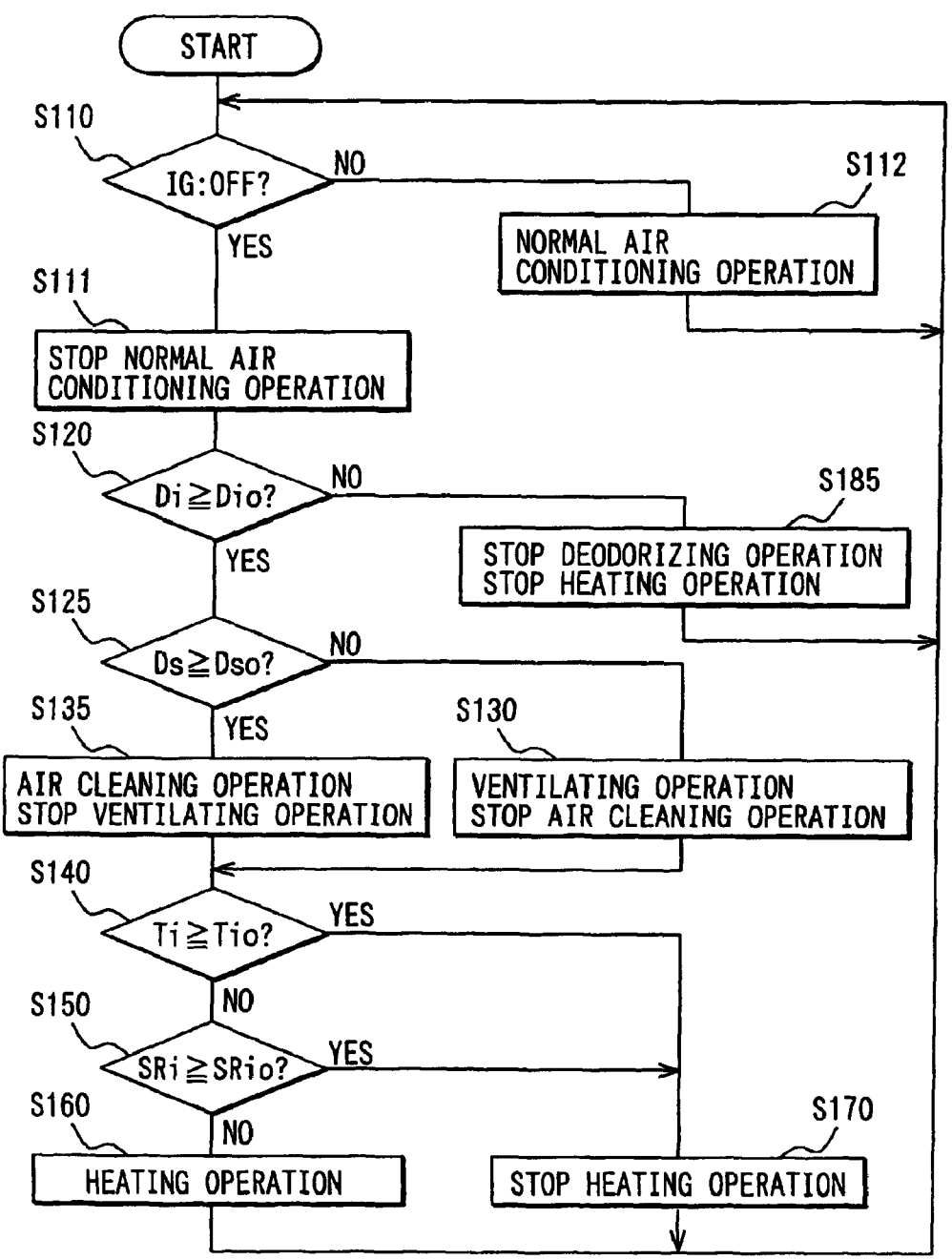
FIG. 7 is a flow chart showing a process of a controller according to the second embodiment of the present invention.

In the embodiment, if the outside air is not clean, the air cleaner 50 is used for the deodorizing operation instead of ventilating the passenger compartment between the inside air and the outside air. Next, the operation of the deodorizing apparatus will be described with reference to FIG. 7. FIG. 7 shows a flow chart of a program executed by the controller 4 during the operation of the controller 4. Steps similar to those of the first embodiment are denoted by the same numerals and those explanations are not repeated.

If it is determined that the density Di of the odor components measured by the odor sensor 3 is equal to or higher than the predetermined density Dio at S120, it is determined whether the density Ds of odor components in the outside air measured by the outside air odor sensor 60 is equal to or higher than a predetermined density Dso of the outside air odor components (e.g. normally between 2.0 ppm and 3.0 ppm) at S125. The predetermined density Dso is recorded in the ROM of the controller 4 beforehand. Thus, the controller 4 reads the predetermined density Dso from the ROM when it makes a determination.

If it is determined that the density Ds of the outside air odor components is equal to or higher than the predetermined density Dso, an air cleaning operation is performed at S135. Specifically, the motor 15 is controlled to drive the fan 11. The motor 54 is controlled to drive the blower 53. The servomotor 28 is controlled to fix the air mixing door 16 at the maximum cooling position. The servomotor 25 is controlled to close the defroster door 22 and the foot door 24 and to open the face door 23. In this way, the air cleaning operation is performed. At S135, if the ventilating operation is performed between the inside air and the outside air by the air conditioning unit 6, it is stopped. That is, the servomotor 27 is controlled to switch the inside/outside air switching door 14 to the position of the inside air mode.

If it is determined that the density Ds of the outside air odor components is lower than the predetermined density Dso at S125, the air conditioning unit 6 is controlled to perform the ventilating operation in a manner similar to the first embodiment at S130. Also, at S130, the air cleaning operation of the air cleaner 50 is stopped if it is performed. Specifically, the motor 54 is controlled to stop the blower 53, so that the operation of the air cleaner 50 is stopped.

If it is determined that the density Di of the inside air is lower than the predetermined density Dio at S120, the deodorizing operation, which includes the ventilating operation and the air cleaning operation, and the heating operation are stopped at S185 if those operations are performed. Specifically, the motor 54 is controlled to stop the blower 53. The motor 15 is controlled to stop the operation of the fan 11. The electric heaters 42, 43 are controlled to stop heating. At this time, the inside/outside air switching door 14, the air mixing door 16, the defroster door 22, the face door 23, and the foot door 24 can be at any positions.

Accordingly, when the density Ds of the outside air odor components is higher than the predetermined density Dso, the passenger compartment is deodorized by the air cleaner 50. The ventilating operation generally provides a deodorizing effect higher than that of the air cleaning operation of the air cleaner 50. Therefore, when the density Ds is lower than the predetermined density Dso, the passenger compartment is deodorized by the ventilating operation of the air conditioning unit 6. In addition to the advantages similar to the first embodiment, the air cleaning operation is performed by the air cleaner 50 if the outside air is polluted. Accordingly, the passenger compartment is effectively deodorized.

[Third Embodiment]

The deodorizing apparatus of the third embodiment differs from that of the first embodiment because it does not have the temperature sensor 2. When the amount SRi of the solar radiation measured by the solar radiation sensor 5 is sufficient, the inside temperature Ti increases as the time elapses. Based on this fact, a timing that the inside temperature Ti reaches the temperature (for example, 35° C. or more) suitable for separating the odor components adhered to the interior of the passenger compartment is estimated. Thus, the ventilating operation is started at the timing. In the embodiment, the timing is set at or after a time predetermined period (for example, more than thirty minutes) elapsed since the vehicle 1 is parked.

Next, the operation of the deodorizing apparatus of the third embodiment will be described with reference to FIG.

Figure 8:
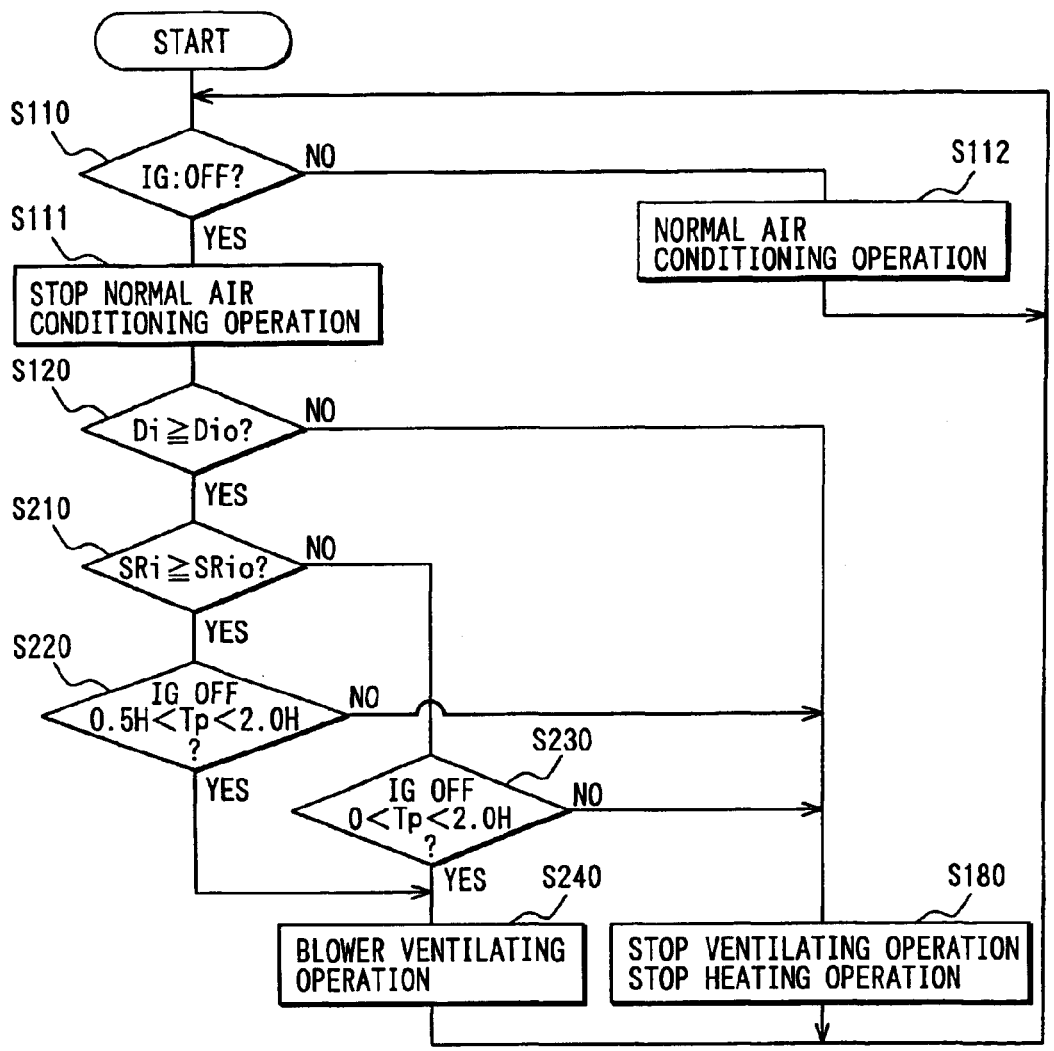
FIG. 8 is a flow chart showing a process of a controller according to the third embodiment of the present invention.

8. FIG. 8 shows a flow chart of a program executed by the controller 4 during the operation of the controller 4. In the flow chart, steps similar to those of the first embodiment in FIG. 4 are denoted with the same numerals and those descriptions are not repeated. Here, the controller 4 is provided with a time clock (not shown) to measure time. Also, the time when the ignition key is turned off lately is recorded and stored on the RAM.

If it is determined that the density Di of the odor components measured by the odor sensor 3 is equal to or higher than the predetermined density Dio at S120, it is determined whether the amount SRi of the solar radiation is equal to or higher than the predetermined amount SRio at S210, in a manner similar to the step S150 of FIG. 4.

If it is determined that the amount SRi of the solar radiation is equal to or higher than the predetermined amount SRio, it is determined whether an elapsed time Tp, which is a period of time elapsed since the ignition key is turned off lately, is within a range between thirty minutes and two hours at S220. If it is determined that the elapsed time Tp is within the range between thirty minutes and two hours, the ventilating operation is performed at S240, in a manner similar to the control of S130 of FIG. 4. Then, the control returns to S110. If it is determined that the elapsed time period Tp is equal to or shorter than thirty minutes or equal to or longer than two hours, the ventilating operation and the heating operation are stopped at S180.

If it is determined that the amount SRi of solar radiation is less than the predetermined amount SRio at S210, it is determined whether the elapsed time Tp is less than two hours at S230. If it is determined that the elapsed time Tp is shorter than two hours, the ventilating operation is performed at S240. On the other hand, if it is determined that the elapsed time Tp is equal to or more than two hours, the ventilating operation is stopped at S180.

Accordingly, when it is determined that the amount SRi of the solar radiation is equal to or higher than the predetermined amount SRio, it is assumed that the inside temperature Ti gradually increases as the time elapses and reaches the predetermined temperature Tio thirty minutes after the vehicle is parked. Thus, the ventilating operation is started thirty minutes after the vehicle 1 is parked.

Accordingly, while the vehicle 1 is parked, the timing to start the deodorizing operation is estimated based on the amount SRi of solar radiation measured by the solar radiation sensor 5. The deodorizing operation by the deodorizing means is started at the timing. Therefore, the passenger compartment is deodorized under the temperature suitable for separating the odor components adhered to the interior of the passenger compartment.

If the amount SRi of solar radiation is not sufficient, it is not assumed that the inside temperature Ti increases to the suitable temperature even if the time elapses after the ignition key off. However, it is assumed that the inside temperature Ti is maintained approximately 25 degrees Celsius by the air conditioning operation when the ignition key is turned off, because the vehicle 1 has been driven until the ignition key is turned off. In this case, the ventilating operation is performed immediately after the ignition key is turned off. Although the inside temperature Ti is lower than the suitable temperature, the ventilating operation can be performed under the temperature even higher than a temperature without air conditioning operation. Thus, the odor components, which are extricating in the compartment at that time, can be eliminated at least.

The ventilating operation is stopped in two hours after the ignition key is turned off, irrespective of the amount SRi of the solar radiation. The two hour period is a maximum period of time of the ventilating operation to prevent excess use of power of the battery.

In this embodiment, the deodorizing operation is performed by the air conditioning unit 6. Similar to the second embodiment, however, the deodorizing operation can be performed by the air cleaner 50.

[Fourth Embodiment]

Figure 9:
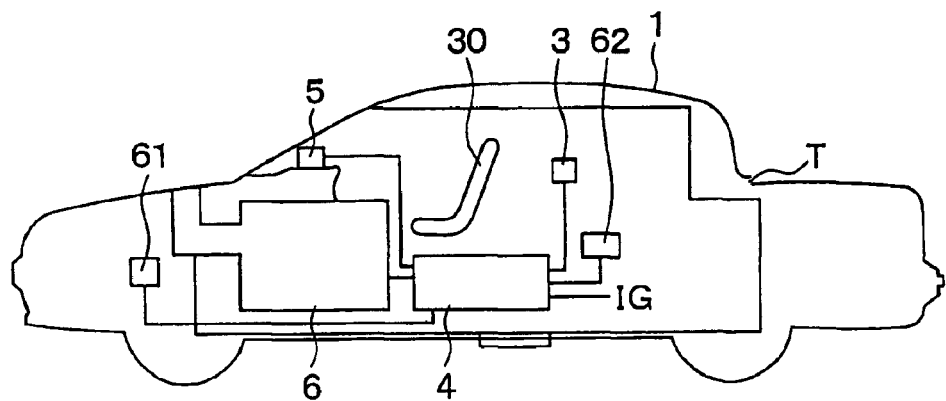
FIG. 9 is a schematic diagram showing an arrangement of a deodorizing apparatus on a vehicle according to the fourth embodiment of the present invention.

Referring to FIG. 9, the fourth embodiment and the third embodiment differs from the third embodiment because the deodorizing apparatus of the fourth embodiment has a battery bolt meter 61 for measuring a voltage Ve of the vehicle battery and a coolant temperature sensor 62 for measuring a temperature Tw of an engine coolant.

Information of physical values measured by the meter 61 and the sensor 62 are sent to the controller 4 as signals. In the embodiment, if the amount SRi of solar radiation is less than the predetermined amount SRio and the increase in the inside temperature Ti by the solar radiation is not assumed, the heating operation is performed. Specifically, when the amount SRi of solar radiation is less than the predetermined amount SRio, the heating operation is performed by the air conditioning unit 6 and the heaters 42, 43 on the basis of the voltage Ve of the battery and the temperature Tw of the engine coolant. Here, a predetermined voltage Veo of the battery and a predetermined temperature Teo of the coolant for this operation are recorded in the ROM of the controller 4.

Figure 10:
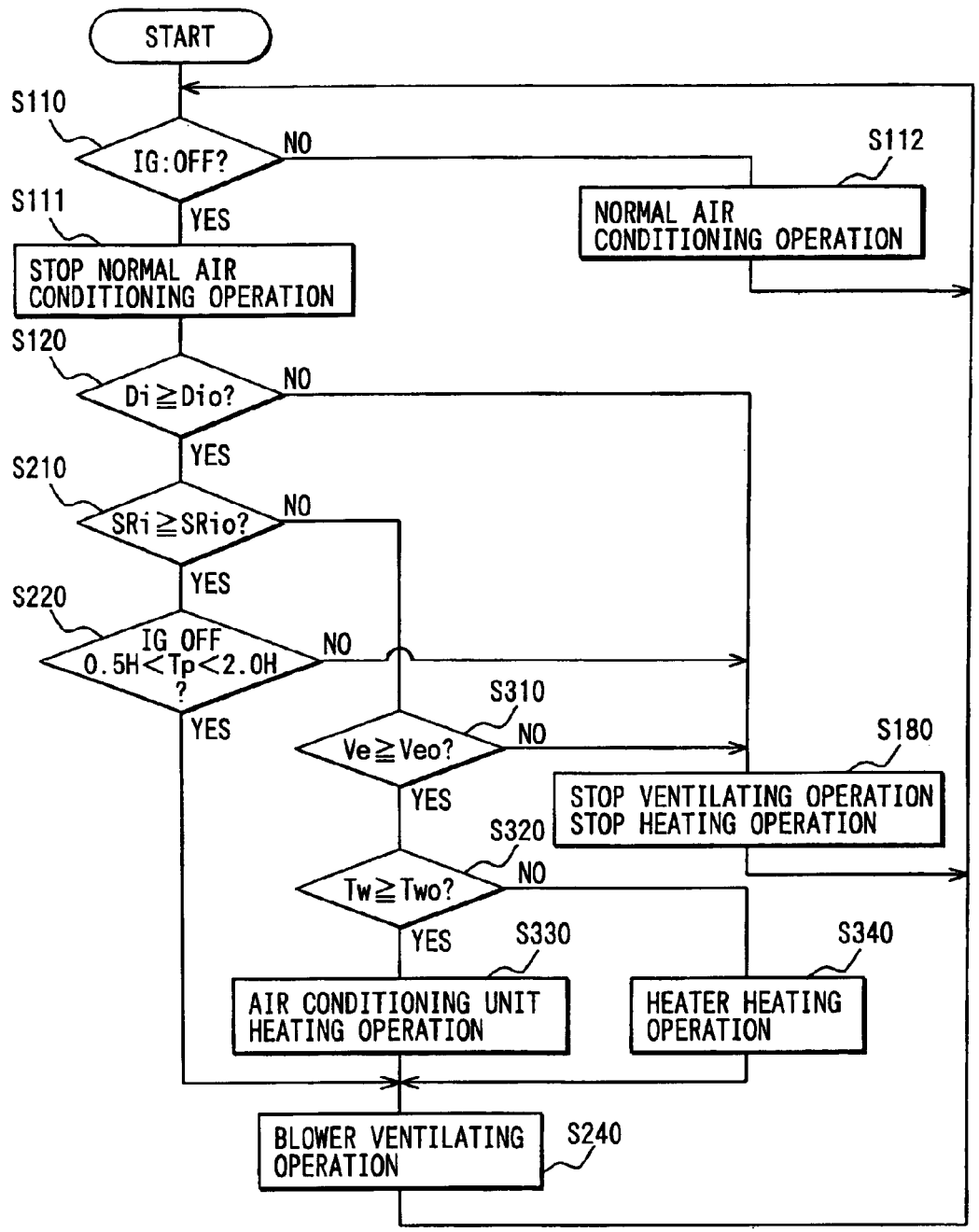
FIG. 10 is a flow chart showing a process of a controller according to the fourth embodiment of the present invention.

Next, the operation of the deodorizing apparatus will be described with reference to FIG. 10. FIG. 10 shows a flow chart of a program executed by the controller 4 during the operation of the controller 4. Here, steps similar to the steps of the third embodiment in FIG. 8 are denoted by the same numerals and those descriptions are not repeated.

If it is determined that the amount SRi of the solar radiation is less than the predetermined amount SRio at S210, it is determined whether the voltage Ve of the battery measured by the voltmeter 61 is equal to or higher than the predetermined voltage Veo (for example, 10.8 V) at S310.

If it is determined that the voltage Ve is lower than the predetermined voltage Veo, the ventilating operation and the heating operation are stopped at S180 if those operations are performed. If it is determined that the voltage Ve is equal to or higher than the predetermined voltage Veo, it is determined whether the temperature Te of the engine coolant measured by the sensor 62 is equal to or higher than the predetermined temperature Teo (for example, 45° C.) at S320.

If it is determined that the temperature Te of the engine coolant is equal to or higher than the predetermined temperature Teo, the air conditioning unit 6 is controlled to perform the heating operation at S330. Specifically, the servomotor 28 is controlled such that the air mixing door 16 is fixed to the position shown by the line B (FIG. 2) so that the air blown by the fan 11 entirely passes through the heater core 17.

If it is determined that the temperature Tw of the engine coolant is lower than the predetermine temperature Two, the heaters 42, 43 are controlled to heat the seat 30 at S340. Specifically, the heaters 42, 43 are controlled to generate heat.

Accordingly, if the voltage Ve of the battery is equal to or higher than the predetermined voltage Veo, it is less likely that the power of the battery is exhausted. Also, when the temperature Tw of the engine coolant is equal to or higher than the predetermined temperature Two, it is assumed that the passenger compartment is sufficiently heated with the heat of the engine coolant. Thus, when those conditions are satisfied, the heating operation is performed by the air conditioning unit 6.

If the voltage Ve of the battery is equal to or higher than the predetermined voltage Veo and the temperature Tw of the engine coolant is lower than the predetermined temperature Two, it is assumed that the heating operation by using the heat of the engine coolant is insufficient for deodorizing the passenger compartment, though the power of the battery is sufficient. In this case, the heating operation is performed by the heaters 42, 43.

If the voltage Ve of the battery is lower than the predetermined voltage Veo, the power of the battery is likely to be exhausted. Therefore, the heating operation is not performed.

Accordingly, the heating operation for separating the odor components adhered to the interior is performed in accordance with the conditions of the temperature of the engine coolant and the power of the battery.

In the above-described embodiments, the ventilating operation of the air conditioning unit 6 and the air cleaner 50 construct the deodorizing devices (deodorizing means). The heating operation of the air conditioning unit 6 and the heaters 42, 43 construct the compartment heating devices.

The ventilating operation control of S130 in FIGS. 4 and 7 and the air cleaning operation control of S135 in FIG. 7 construct deodorizing operation control procedure (deodorizing operation control means) for controlling the deodorizing means to remove the odor components in the compartment, when the vehicle 1 is parked and the inside temperature Ti measured by the temperature sensor 2 is equal to or higher than the predetermined temperature Tio. This is because the ventilating operation is maintained in the control from S140 to S170. The control of S130 in FIG. 4 can be performed just before and just after the control of S170.

The control of S160 in FIGS. 4 and 7 constructs a heating operation control procedure (heating operation control means) for controlling the compartment heating devices to heat the passenger compartment, when the vehicle 1 is parked and the inside temperature Ti is lower than the predetermined temperature Tio.

The controls of S150 and S170 in FIGS. 4 and 7 and the controls of S210 and S220 in FIGS. 8 and 10 construct deodorizing timing estimating procedure (estimating means) for estimating the timing that the inside temperature Ti reaches the predetermined temperature, that is, the timing to start the deodorizing operation. The timing is estimated on the basis of the amount SRi of the solar radiation measured by the solar radiation sensor 5. Alternatively, the timing is for example estimated based on an outside temperature outside the passenger compartment, which is measured by an outside temperature sensor. The outside temperature is measured and sent to the controller 4. Specifically, at S150 in FIGS. 4 and 7 and S210 in FIGS. 8 and 10, the determination can be made whether the amount SRi of solar radiation is equal to or higher than the predetermined amount SRio and the outside temperature is equal to or higher than a predetermined temperature (e.g. 25° C.).

The controls of S240 in FIGS. 8 and 10 construct the deodorizing operation control procedure (deodorizing operation control means) for controlling the deodorizing means to remove the odor components in the passenger compartment when the vehicle is parked and the condition for the deodorizing operation, which is estimated by the deodorization condition estimating means, is satisfied.

Further, in the above-described embodiments, the deodorizing operation is performed when it is determined that the density Di of the odor components is equal to or higher than the predetermined density Dio. In addition to this, for example, the deodorizing operation can be always performed until a total travel distance reaches a predetermined distance, for example, 6000 km. Alternatively, the deodorizing operation can be always performed during a predetermined period of time, for example, a half year after the purchase of the vehicle. Because a large amount of odor components such as VOC (volatile organic compound) is adhered to the vehicle within about the half year after the purchase, it is preferable to perform the deodorizing operation as long as possible. The threshold of 6000 km is decided in a point of view that the travel distance may reach 6000 km in a half year after the purchase.

At S120 in FIGS. 4, 7, 8 and 10, the determination of the density of the odor components can be made by comparing the density Di measured by the odor sensor 3 to the prior density. For example, it can be determined whether the present density Di is increased equal to or more than 15% with respect to an average density of prior four years.

At S110 in FIGS. 4, 7, 8, and 10, whether the vehicle 1 is parked is determined based on the state of the ignition key. Alternatively, the determination that the vehicle 1 is parked can be determined based on another standard.

The first blower unit 33 and the second blower unit 34 can be connected to the air outlet port of the air conditioning unit 6 through ducts so that the outside air is introduced in the first blower unit 33 and the second blower unit 34 and blown into the compartment from the openings 37, 40 of the seat 30. In this case, the ventilating operation for ventilating the air between the outside air and the inside air can be performed by the first blower unit 33 and the second blower unit 34. Thus, the first blower unit 33 and the second blower unit 34 construct the deodorizing means.

The present invention should not be limited to the disclosed embodiments, but may be implemented in other ways without departing from the spirit of the invention.

What is claimed is:

1. A deodorizing apparatus for a passenger compartment of a vehicle comprising:

a temperature sensor that measures an inside temperature inside the passenger compartment;

a deodorizing means for removing odor components in the passenger compartment;

a compartment heating device that heats an inside of the passenger compartment;

a deodorizing operation control means for controlling the deodorizing means to remove odor components in the passenger compartment when the vehicle is parked and the measured inside temperature is equal to or higher than a predetermined temperature, which is on a level suitable for separating odor components adhered to an interior of the passenger compartment; and a heating operation control means for controlling the compartment heating device to heat the inside of the passenger compartment so that the inside temperature is equal to or higher than the predetermined temperature when the vehicle is parked and the measured inside temperature is lower than the predetermined temperature.

2. The deodorizing apparatus according to claim 1, wherein the heating device includes an electric heater that is disposed in a vehicle seat.

3. The deodorizing apparatus according to claim 1, further comprising:

an odor sensor that measures a density of the odor components in the passenger compartment, wherein when it is determined that the measured density of the odor components is equal to or higher than a predetermined density and the measured inside temperature is equal to or higher than the predetermined temperature while the vehicle is parked, the deodorizing operation control means controls the deodorizing means to remove the odor components from the passenger compartment, and wherein when it is determined that the measured density of the odor components is equal to or higher than the predetermined density and the measured inside temperature is lower than the predetermined temperature while the vehicle is parked, the heating operation control means controls the heating device to heat the passenger compartment so that the inside temperature is equal to or higher than the predetermined temperature.

4. The deodorizing apparatus according to claim 1, wherein the deodorizing means is constructed of a blower that performs ventilation of the air inside the passenger compartment.

5. The deodorizing apparatus according to claim 1, wherein the deodorizing means is constructed of an air cleaner for the passenger compartment.

6. A deodorizing apparatus for a passenger compartment of a vehicle comprising:
   an estimating means for estimating a timing that an inside temperature inside the passenger compartment is equal to or higher than a predetermined temperature for separating odor components adhered to an inside of the passenger compartment;
   a deodorizing means for removing odor components in the passenger compartment; and
   a deodorizing operation control means for controlling the deodorizing means so that the deodorizing means starts to remove the odor components in the passenger compartment at the timing, while the vehicle is parked.

7. The deodorizing apparatus according to claim 6, further comprising:
   a solar radiation sensor that measures an amount of solar radiation to the vehicle,
   wherein when it is determined that the measured amount of solar radiation is equal to or higher than a predetermined amount, the estimating means estimates the timing at a time predetermined period elapsed since the vehicle is parked.

8. The deodorizing apparatus according to claim 6, further comprising:
   an odor sensor that measures a density of the odor components in the passenger compartment;
   wherein when the vehicle is parked and it is determined that the measured density of the odor components is equal to or higher than a predetermined density, the deodorizing operation control means controls the deodorizing means so that the deodorizing means starts to remove the odor components at the timing.

9. The deodorizing apparatus according to claim 6, wherein the deodorizing means is constructed of a blower that performs ventilation of the air.

10. The deodorizing apparatus according to claim 6, wherein the deodorizing means is constructed of an air cleaner for the passenger compartment.

11. A method for deodorizing a passenger compartment of a vehicle comprising;
   determining whether an inside temperature inside the passenger compartment is equal to or higher than a predetermined temperature while the vehicle is parked;
   controlling a deodorizing means to remove odor components in the passenger compartment when it is determined that the inside temperature is equal to or higher than the predetermined temperature; and
   controlling a heating device to heat the passenger compartment when it is determined that the inside temperature is lower than the predetermined temperature, so that the inside temperature reaches the predetermined temperature.

12. The method according to claim 11, further comprising:
   determining whether a density of odor components in the passenger compartment measured by an odor sensor is equal to or higher than a predetermined density,
   wherein when the measured density is equal to or higher than the predetermined density, it is determined that the measured inside temperature is equal to or higher than the predetermined temperature.

13. A method for deodorizing a passenger compartment of a vehicle comprising:
   estimating a timing that an inside temperature inside the passenger compartment reaches a predetermined temperature, while the vehicle is parked; and
   controlling a deodorizing means so that the deodorizing means starts to remove odor components in the passenger compartment at the timing.

14. The method according to claim 13, further comprising:
   determining whether an amount of solar radiation to the passenger compartment measured by a solar radiation sensor is equal to or higher than a predetermined amount,
   wherein when the measured amount of solar radiation is equal to or higher than the predetermined amount, the estimating means estimates the timing at a time predetermined period elapsed since the vehicle is parked.

15. The method according to claim 13, further comprising:
   determining whether a density of odor components in the passenger compartment measured by an odor sensor is equal to or higher than a predetermined density,
   wherein when it is determined that the measured density is equal to or higher than the predetermined density, the deodorizing means is controlled to start to remove the odor components at the timing.

* * * * *